United States Patent
Onishi et al.

(10) Patent No.: US 10,561,828 B2
(45) Date of Patent: Feb. 18, 2020

(54) TREATMENT TOOL FOR ENDOSCOPE

(71) Applicant: OLYMPUS CORPORATION, Hachioji-shi, Tokyo (JP)

(72) Inventors: Koji Onishi, Tokyo (JP); Masaru Yuasa, Tokyo (JP); Koji Miyake, Tokyo (JP); Norichika Fukushima, Tokyo (JP); Shunsuke Miyauchi, Tokyo (JP)

(73) Assignee: OLYMPUS CORPORATION, Tokyo (JP)

( * ) Notice: Subject to any disclaimer, the term of this patent is extended or adjusted under 35 U.S.C. 154(b) by 220 days.

(21) Appl. No.: 15/874,608

(22) Filed: Jan. 18, 2018

(65) Prior Publication Data

US 2018/0140812 A1  May 24, 2018

Related U.S. Application Data

(63) Continuation of application No. PCT/JP2016/064584, filed on May 17, 2016.

(30) Foreign Application Priority Data

Jul. 22, 2015  (JP) .................................. 2015-144767

(51) Int. Cl.
*A61M 29/02*  (2006.01)
*A61M 25/10*  (2013.01)
(Continued)

(52) U.S. Cl.
CPC ........ *A61M 29/02* (2013.01); *A61M 25/0662* (2013.01); *A61M 25/1002* (2013.01);
(Continued)

(58) Field of Classification Search
CPC .......... A61M 25/1034; A61M 25/0102; A61M 25/0108; A61M 25/0662; A61M 25/1002;
(Continued)

(56) References Cited

U.S. PATENT DOCUMENTS

| 2005/0197668 A1 | 9/2005 | Lim et al. |
| 2007/0100280 A1 | 5/2007 | van Sloten et al. |

(Continued)

FOREIGN PATENT DOCUMENTS

| JP | S57-023506 B2 | 5/1982 |
| JP | 2000-051361 A | 2/2000 |

(Continued)

OTHER PUBLICATIONS

Aug. 2, 2016 Search Report issued in International Patent Application No. PCT/JP2016/064584.
(Continued)

*Primary Examiner* — Jocelin C Tanner
(74) *Attorney, Agent, or Firm* — Oliff PLC

(57) ABSTRACT

A treatment tool for an endoscope of the present invention includes a sheath, a balloon provided at the sheath and configured to be expandable to an inflated state from a reduced diameter state by injecting a fluid, a shaft member inserted through an inside of the balloon and configured to extend along a longitudinal axis of the sheath from a distal end of the balloon to a proximal end thereof, and an adhering portion provided on a side of an inner surface of a central portion of the balloon in a direction of the longitudinal axis, formed of an adhering material applied or adhered to the shaft member and configured to hold the central portion in a state in which the central portion is reduced in diameter.

9 Claims, 10 Drawing Sheets

(51) Int. Cl.
*A61M 25/06* (2006.01)
*A61M 25/01* (2006.01)

(52) U.S. Cl.
CPC ............... *A61M 25/10182* (2013.11); *A61M 25/10184* (2013.11); *A61M 25/0102* (2013.01); *A61M 25/0108* (2013.01); *A61M 2025/1004* (2013.01); *A61M 2205/3344* (2013.01); *A61M 2205/583* (2013.01); *A61M 2210/105* (2013.01)

(58) Field of Classification Search
CPC ...... A61M 25/10182; A61M 25/10184; A61M 29/02; A61M 2025/0186; A61M 2025/1004; A61M 2025/1059; A61M 2025/1079; A61M 2025/1061; A61M 2025/1065; A61M 2025/1072; A61M 2025/1095; A61M 2025/1097; A61M 2205/3344; A61M 2205/583; A61M 2210/105
See application file for complete search history.

(56) References Cited

U.S. PATENT DOCUMENTS

| | | |
|---|---|---|
| 2009/0054837 A1 | 2/2009 | Von Holst et al. |
| 2014/0277053 A1 | 9/2014 | Wang et al. |
| 2014/0277069 A1* | 9/2014 | Bhagchandani .... A61M 25/104 606/194 |
| 2015/0045826 A1 | 2/2015 | Drasler et al. |
| 2015/0174383 A1* | 6/2015 | Tsutsui .............. A61M 25/1029 604/103.07 |
| 2015/0217093 A1 | 8/2015 | Tsutsui et al. |

FOREIGN PATENT DOCUMENTS

| | | |
|---|---|---|
| JP | 2002-539902 A | 11/2002 |
| JP | 2006-502799 A | 1/2006 |
| JP | 2006-508702 A | 3/2006 |
| JP | 2009-525790 A | 7/2009 |
| JP | 2010-004915 A | 1/2010 |
| JP | 2011-504130 A | 2/2011 |
| JP | 2011-513004 A | 4/2011 |
| JP | 2012-505050 A | 3/2012 |
| JP | 2014-124264 A | 7/2014 |
| JP | 2014-124265 A | 7/2014 |
| WO | 00/57945 A2 | 10/2000 |
| WO | 03/084594 A2 | 10/2003 |
| WO | 2004/035127 A1 | 4/2004 |
| WO | 2009/066330 A1 | 5/2009 |
| WO | 2009/111712 A1 | 9/2009 |
| WO | 2010/042869 A1 | 4/2010 |
| WO | 2015/146259 A1 | 10/2015 |

OTHER PUBLICATIONS

May 23, 2017 Office Action issued in Japanese Patent Application No. 2017-507459.
Mar. 14, 2019 Extended Search Report issued in European Patent Application No. 16827497.5.

* cited by examiner

TREATMENT TOOL FOR ENDOSCOPE

This application is a continuation application based on PCT Patent Application No. PCT/JP2016/064584, filed May 17, 2016, claiming priority based on Japanese Patent Application No. 2015-144767, filed Jul. 22, 2015, the content of which is incorporated herein by reference.

BACKGROUND OF THE INVENTION

Field of the Invention

The present invention relates to a treatment tool for an endoscope used when performing a dilation treatment on a stenosed portion or an occluded portion of a luminal organ in a living body.

Description of the Related Art

Conventionally, a procedure for performing a dilation treatment or the like of a stenosed portion or an occluded portion (hereinafter referred to as "stenosed portion or the like") of a digestive tract while using an endoscope is performed. In such a procedure, for example, a treatment tool for an endoscope equipped with a balloon is used. Specifically, the endoscope and the treatment tool for the endoscope are inserted into a luminal organ in a living body together, and the balloon is inflated while the balloon is inserted into the stenosed portion or the like to dilate the stenosed portion or the like. When the treatment tool for the endoscope is disposed to dilate the stenosed portion or the like of the luminal organ in the living body in this manner, the balloon may slip against the stenosed portion or the like while the balloon is inflated, and the balloon may become detached from a position to be dilated. In this case, it is necessary for a surgeon to temporarily deflate the balloon and perform positioning of the balloon again, which makes an operation complicated.

Therefore, to prevent the balloon from slipping on the stenosed portion or the like and being displaced from its position when the balloon inflates, a treatment tool for an endoscope using a balloon in which a small diameter portion is formed between a distal end portion and a proximal end portion when the balloon inflates has been proposed (refer to, for example, PCT International Publication No. WO2010/042869, Japanese Unexamined Patent Application, First Publication No. 2010-4915, and PCT International Publication No. WO00/57945).

SOLUTION TO PROBLEM

A treatment tool for an endoscope according to a first aspect of the present invention includes a sheath, a balloon provided at the sheath and configured to be expandable to an inflated state from a reduced diameter state by injecting a fluid, a shaft member inserted through an inside of the balloon and configured to extend along a longitudinal axis of the sheath from a distal end of the balloon to a proximal end thereof, and an adhering portion provided on a side of an inner surface of a central portion of the balloon in a direction of the longitudinal axis, formed of an adhering material applied or adhered to the shaft member and configured to hold the central portion in a state in which the central portion is reduced in diameter, wherein the balloon is configured so that, when the fluid is injected and an internal pressure of the balloon is equal to or lower than a first internal pressure, the inner surface of the central portion is stuck to the shaft member by the adhering material, and only a distal end portion located on a distal end side from the central portion, and a proximal end portion located on a proximal end side from the central portion inflate so that a difference between an outer diameter of each of the distal end portion and the proximal end portion and, an outer diameter of the central portion increases, and when the internal pressure of the balloon is higher than the first internal pressure, the central portion is peeled off from the adhering portion, a state in which the central portion is reduced in diameter is released, the central portion increases in diameter, and thus the balloon has a substantially cylindrical shape.

A treatment tool for an endoscope according to a second aspect of the present invention includes a sheath, a balloon provided at the sheath and configured to be expandable to an inflated state from a reduced diameter state by injecting a fluid, and an adhering portion provided on a side of an inner surface of a central portion in a direction of a longitudinal axis of the sheath, and configured to hold the central portion in a state in which the central portion is reduced in diameter, wherein the inflated state is a state in which folds of a distal end portion, a proximal end portion and the central portion are released, wherein the reduced diameter state is a state in which the distal end portion, the proximal end portion and the central portion of the balloon are folded, and wherein the balloon is configured so that, when the fluid is injected and an internal pressure of the balloon is equal to or lower than a first internal pressure, sticking of the central portion and the adhering portion is held, and only the distal end portion and the proximal end portion inflate, when the internal pressure of the balloon is higher than the first internal pressure, the adhering portion is peeled off, the central portion inflates, and thus the balloon expands to the inflated state, and when the fluid is further injected and the internal pressure is increased in the inflated state, a film constituting the balloon is stretched, and thus the distal end portion, the proximal end portion and the central portion further inflate.

As a third aspect of the present invention, in the treatment tool for the endoscope according to the first aspect, when the balloon returns to the reduced diameter state after the adhering material is peeled off from the balloon, the adhering material may be stuck again to the balloon and may hold the central portion in a state in which the central portion is reduced in diameter.

As a fourth aspect of the present invention, in the treatment tool for the endoscope according to the first aspect, the shaft member may have a first port and a second port configured to inject the fluid injected from the sheath into the balloon, the first port may be located on a proximal end side from the adhering portion in the direction of the longitudinal axis, and the second port may be located on a distal end side from the adhering portion in the direction of the longitudinal axis.

As a fifth aspect of the present invention, in the treatment tool for the endoscope according to the first aspect, a marker may be provided at an end portion of the central portion of the balloon in the direction of the longitudinal axis.

As a sixth aspect of the present invention, in the treatment tool for the endoscope according to the first aspect, the reduced diameter state may be a state in which the distal end portion, the proximal end portion and the central portion of the balloon are folded, the inflated state may be a state in which folds of the distal end portion, the proximal end portion and the central portion of the balloon are released, and the balloon increases in diameter due to the release of the folds until reaching the inflated state, and when the fluid is further injected and the internal pressure is increased in the inflated state, a film constituting the balloon may be stretched, and thus the distal end portion, the proximal end portion and the central portion may further inflate.

As a seventh aspect of the present invention, in the treatment tool for the endoscope according to the second aspect, when the balloon returns to the reduced diameter state after the adhering portion is peeled off from the balloon, the adhering portion may be stuck again to the balloon and may hold the central portion in a state in which the central portion is reduced in diameter.

As an eighth aspect of the present invention, in the treatment tool for the endoscope according to the second aspect may further include a shaft member inserted through an inside of the balloon and configured to extend along the longitudinal axis from a distal end of the balloon to a proximal end thereof, the adhering portion may be applied or adhered to the shaft member, the shaft member may have a first port and a second port configured to inject the fluid injected from the sheath into the balloon, the first port may be located on a proximal end side from the adhering portion in the direction of the longitudinal axis, and the second port may be located on a distal end side from the adhering portion in the direction of the longitudinal axis.

As a ninth aspect of the present invention, in the treatment tool for the endoscope according to the second aspect, a marker may be provided at an end portion of the central portion of the balloon in the direction of the longitudinal axis.

DETAILED DESCRIPTION OF THE PREFERRED EMBODIMENTS

First Embodiment

Figure 1:
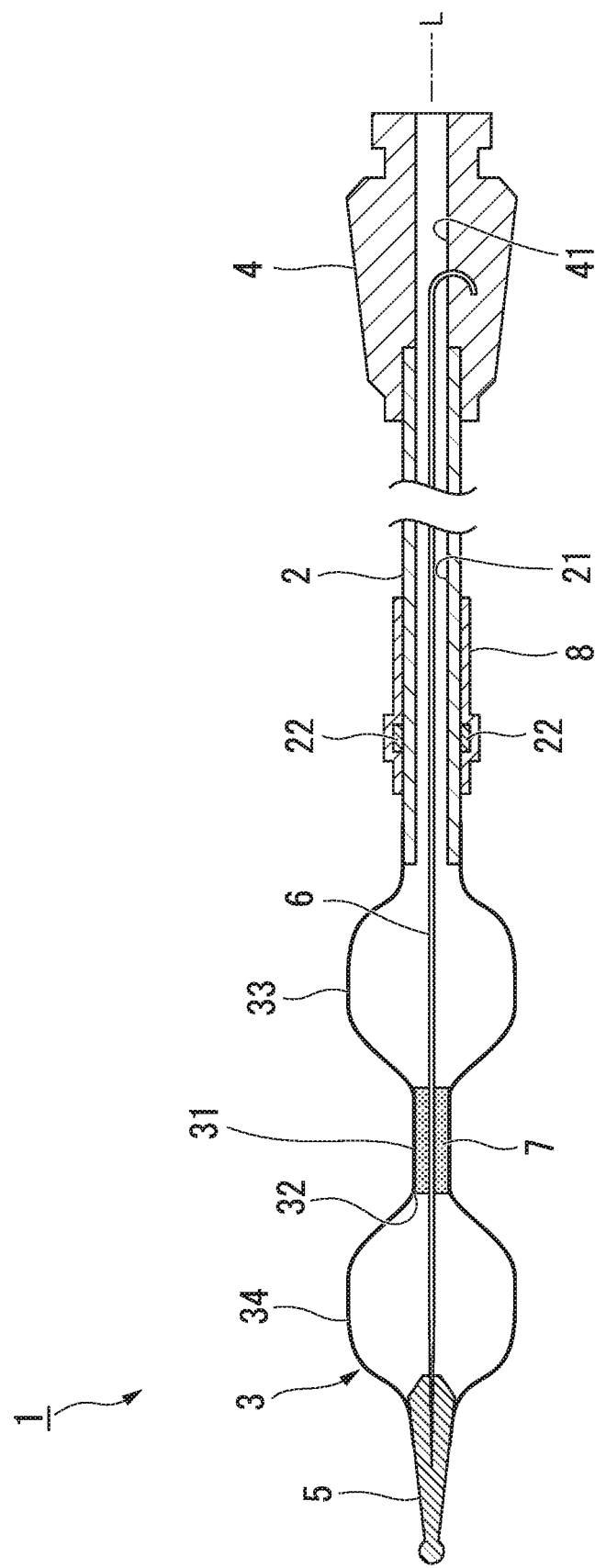
FIG. 1 is a cross-sectional view illustrating a treatment tool for an endoscope according to a first embodiment of the present invention.

A treatment tool for an endoscope according to a first embodiment of the present invention will be described. FIG. 1 is a cross-sectional view of the treatment tool for the endoscope 1 in a direction of a longitudinal axis L. The treatment tool for the endoscope 1 includes a sheath 2, a balloon 3, a connecting portion 4, a distal end tip 5, a stylet (shaft member) 6, and an adhering portion 7.

The sheath 2 has a lumen 21, and is a long and flexible member extending in the direction of the longitudinal axis L. A proximal end portion of the balloon 3 is provided at a distal end portion of the sheath 2. The connecting portion 4 is provided at a proximal end portion of the sheath 2. A communication passage 41 which communicates from a distal end to a proximal end along the longitudinal axis L is formed in the connecting portion 4. The lumen 21 of the sheath 2 communicates with an inside of the balloon 3 and the communication passage 41 of the connecting portion 4. A marker 22 capable of being confirmed under X-ray fluoroscopy and a visual marker 8 capable of being visually recognized by an imaging part 103 (refer to FIG. 2) of an endoscope 100 are provided at the distal end portion of the sheath 2.

The balloon 3 is a bag-shaped member formed of, for example, a transparent film (for example, PEBAX (registered trademark) manufactured by ARKEMA Co.) made of a polyamide-based resin. The balloon 3 is configured to inflate in a substantially cylindrical shape (inflated state) when a fluid is injected and to be capable of deflating in a dimension in a radial direction before the fluid is injected and when the fluid is removed. The balloon 3 is configured so that a wing-shaped portion 35 (refer to FIG. 6) is formed by being folded along a folding line applied in advance when the fluid is not injected. In an initial state, the balloon 3 is folded to have a plurality of wing shapes. This state is referred to as a reduced diameter state. In the balloon 3, the portion folded in the wing shape is released by injection of the fluid, is restored to a shape before a diameter reduction and thus is in the inflated state. In the inflated state, when a predetermined internal pressure or more is further applied, the film forming the balloon 3 inflates while stretching.

The distal end tip 5 is provided at a distal end of the treatment tool for the endoscope 1. The distal end tip 5 is a substantially conical member extending in the direction of the longitudinal axis L, and a distal end portion thereof is formed in a spherical shape to prevent damage to a tissue when the distal end tip 5 is inserted into a body cavity.

The distal end portion of the balloon 3 is in close contact with and fixed to a proximal end portion of the distal end tip 5. The proximal end portion of the balloon 3 is fixed in a state in which the proximal end portion of the balloon 3 is in close contact with the distal end portion of the sheath 2 while the inside of the balloon 3 and the lumen 21 communicate with each other. The balloon 3 communicates with the lumen 21, and a portion thereof other than the portion communicating with the lumen 21 forms a closed space. Therefore, the balloon 3 is configured to inflate when the fluid is injected into the balloon 3 via the lumen 21 and the communication passage 41.

The stylet 6 is a shaft member, is inserted through the inside of the balloon 3 and extends along the longitudinal axis L from the distal end of the balloon 3 to the proximal end thereof. A distal end portion of the stylet 6 is connected to the proximal end of the distal end tip 5. The stylet 6 extends through the inside of the balloon 3, the lumen 21 of the sheath 2 and the communication passage 41 of the connecting portion 4 and is fixed to an inner wall of the communication passage 41 of the connecting portion 4. The stylet 6 is formed of, for example, stainless steel, a nickel-titanium alloy or the like.

The adhering portion 7 is provided inside the balloon 3 to hold a central portion 31 in a state in which the central portion 31 is reduced in diameter. The adhering portion 7 is provided at a position at which the adhering portion 7 is capable of adhering to an inner surface 32 of the central portion 31 in the direction of the longitudinal axis L of the balloon 3. Specifically, the adhering portion 7 is provided by applying an adhering material on an outer circumferential surface of the stylet 6 located inside the balloon 3 at a position at which the position thereof in the direction of the longitudinal axis L is substantially the same as the central portion 31 of the balloon 3. The adhering portion 7 is configured so that the adhering portion 7 is brought into close contact only with the central portion 31, and a proximal end portion 33 on a proximal end side from the central portion 31 and a distal end portion 34 on a distal end side from the central portion 31 are not in contact with the adhering portion 7 in the reduced diameter state of the balloon 3.

Here, adhering means a stuck state in which an inner surface of the balloon 3 and the adhering portion 7 are kept in close contact with each other in a state in which the balloon 3 is disposed close to a member such as the stylet 6 disposed inside the balloon 3 or another portion of the balloon 3 through the adhering portion 7 and the balloon 3 is peeled off from the adhering portion 7 when a force greater than or equal to a predetermined value is applied in a direction away from the adhering portion 7 by application of an external force to the balloon 3. Further, the adhering referred to here includes both a case (adhering) in which peeling and sticking are performed a plurality of times and a case (bonding) in which the balloon 3 may not be stuck once it is peeled off from the adhering portion 7. In the former case, after the balloon 3 is peeled off from the adhering portion at the time of inflation of the balloon 3, when the balloon 3 deflates, the balloon 3 and the adhering portion 7 are adhered and stuck to each other again. Accordingly, when the balloon 3 inflates and deflates, the sticking and the peeling may be repeatedly performed.

In the embodiment, since the stylet 6 is formed of stainless steel and the balloon 3 is formed of a polyamide-based resin, it is preferable to use an adhering material having high adhering strength to stainless steel. This prevents the adhering portion 7 from being stuck to a side of the inner surface 32 of the balloon 3 when the reduced diameter state of the balloon 3 is released. Therefore, in a state in which the balloon 3 inflates in a stenosed portion 301 or the like (refer to FIG. 3), when a state of the stenosed portion 301 or the like is observed through the balloon 3 by the imaging part 103 (refer to FIG. 2) provided at a distal end portion of the endoscope 100, it is possible to prevent the observation by the imaging part 103 of the endoscope 100 from being disturbed by the adhering portion 7. In addition, by performing a modification treatment such as an adjustment of roughness of a surface of the stylet 6 or by increasing the adhering strength between the stylet 6 and the adhering material, it is also possible to maintain the stuck state between the adhering portion 7 and the stylet 6 during the expansion process of the balloon 3 and also to prevent the adhering portion 7 from being stuck to the side of the inner surface 32 of the balloon 3.

As the adhering material forming the adhering portion 7, for example, rubber-based, acrylic-based, silicone-based, urethane-based adhering materials may be used. A material of the adhering material may be appropriately selected according to a region to be performed a procedure using the treatment tool for the endoscope 1, a type of a fluid to be injected into the balloon 3, a material of the balloon 3, and so on.

When water is used as a fluid for inflating the balloon 3, it is more preferable that the adhering portion 7 be formed of a water-insoluble material. As a water-insoluble adhering material, for example, a silicone-based adhering material may be used.

Although the adhering portion 7 is provided inside the balloon 3, it is preferable that the adhering portion 7 be formed of a biocompatible adhering material to prepare for a situation in which the balloon 3 breaks inside a human body. As the biocompatible adhering material, for example, a silicone-based adhering material may be used.

The adhering portion 7 is preferably colorless and transparent from a viewpoint of securing a visual field of the stenosed portion 301 or the like by the endoscope. As an adhering material excellent in transparency, an acrylic-based adhering material may be used.

From the viewpoints of heat resistance and chemical resistance, the adhering portion 7 is preferably a silicone-based adhering material.

From the viewpoints of adhesion and re-peel property, the adhering portion 7 is preferably a urethane-based adhering material.

Further, when the fluid injected into the balloon 3 is water, it is preferable that the adhering material be formed of a material having a refractive index between a refractive index of distilled water and a refractive index of the film of the balloon 3. As a result, it is possible to prevent the adhering material from interfering with the visual field when the stenosed portion 301 or the like is observed by the imaging part 103 of the endoscope 100 in a state in which the balloon 3 inflates. Also, since the fluid is not limited to water, the refractive index or the like of the adhering material may be set according to the refractive index of the fluid to be used.

Figure 3:
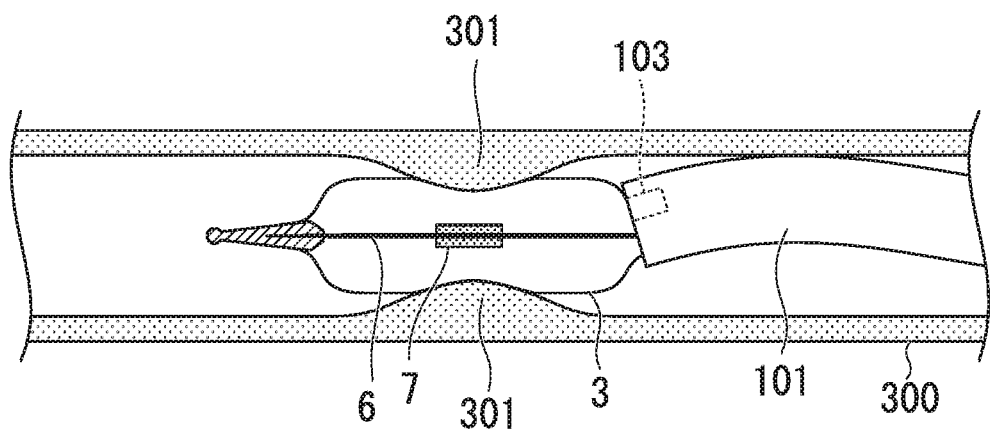
FIG. 3 is a view illustrating the usage mode of the treatment tool for the endoscope according to the first embodiment of the present invention.

FIG. 3 is a view illustrating a usage mode of the treatment tool for the endoscope 1 according to the first embodiment of the present invention. Next, a method of using the treatment tool for the endoscope 1 and a process in which the balloon 3 expands from the reduced diameter state will be described by exemplifying a case in which the treatment tool for the endoscope 1 is applied to an endoscopic dilation operation for the stenosed portion 301 of an esophagus 300.

Figure 2:
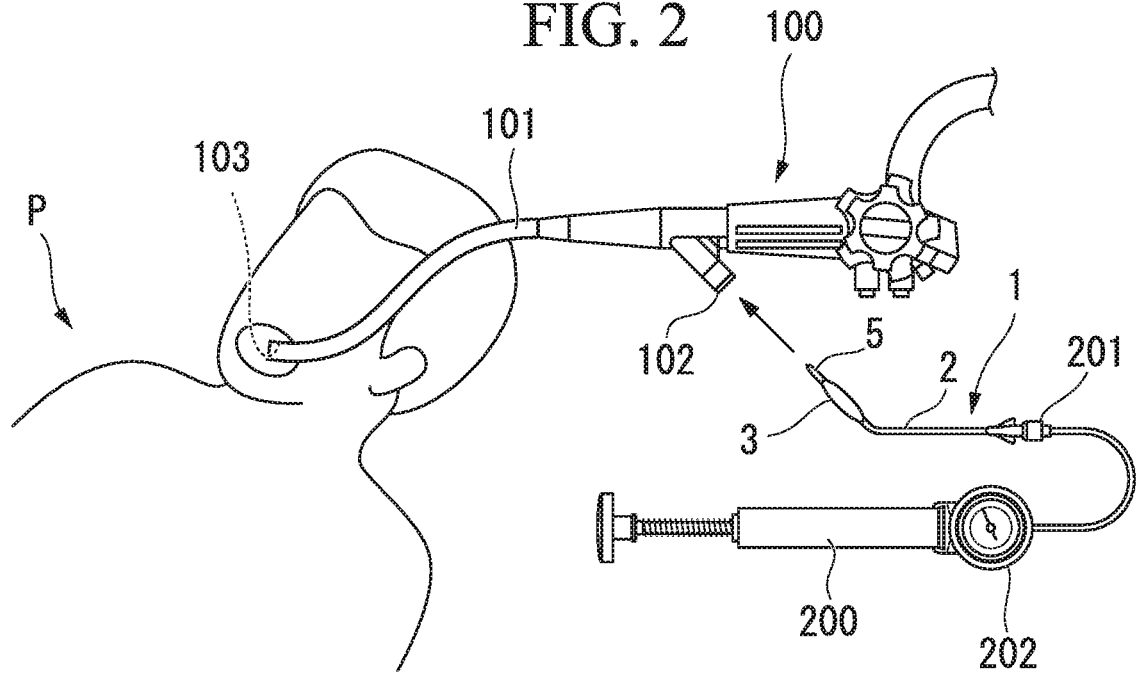
FIG. 2 is a view illustrating a usage mode of the treatment tool for the endoscope according to the first embodiment of the present invention.

FIG. 2 is an overall view illustrating an example of the usage mode of the treatment tool for the endoscope 1 according to the present embodiment. As illustrated in FIG. 2, the treatment tool for the endoscope 1 is used by inserting the balloon 3 and the sheath 2 from a forceps opening 102 into an insertion portion 101 of the endoscope 100 to be inserted into a body of a patient P and then inserting it into the body cavity. The connecting portion 4 is connected to an inflator 200 via a cap 201. The treatment tool for the endoscope 1 is configured that the fluid is injected from the inflator 200 into the balloon 3 via the communication passage 41 and the lumen 21 so that the balloon 3 inflates. The inflator 200 may also suction the fluid in the balloon 3.

Figure 4:
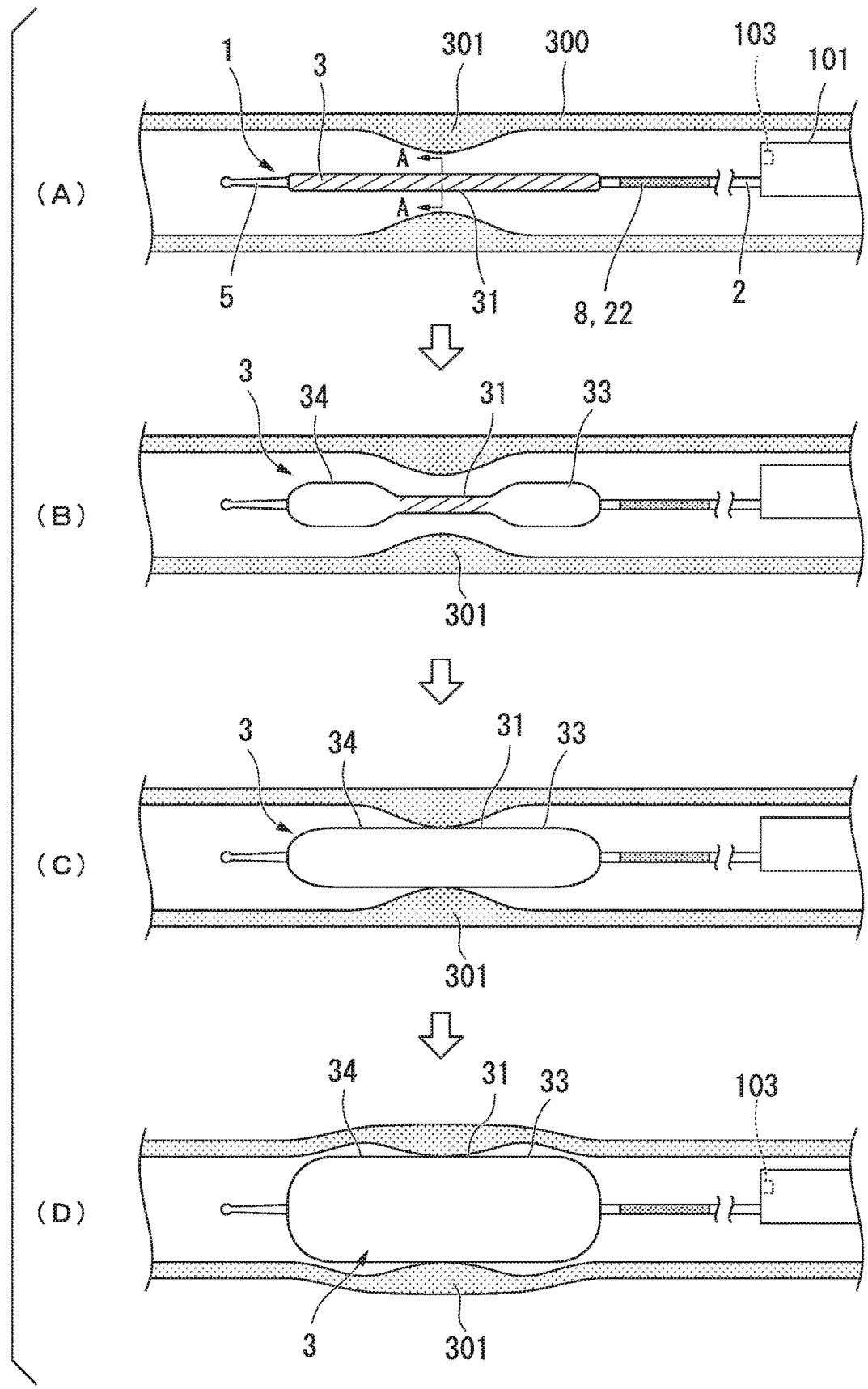
FIG. 4 is a view illustrating an inflation process of a balloon of the treatment tool for the endoscope according to the first embodiment of the present invention.
Figure 5:
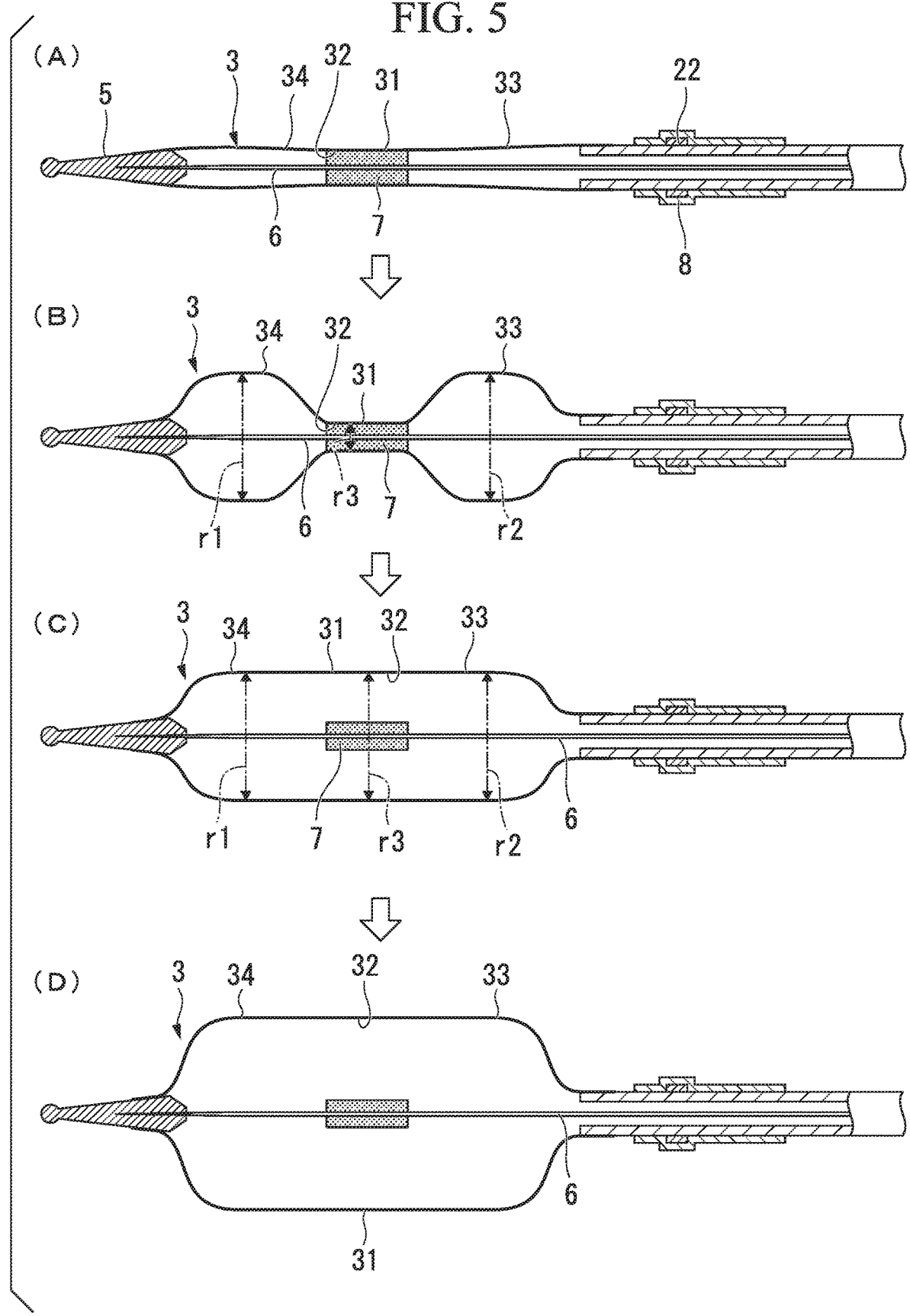
FIG. 5 is a cross-sectional view illustrating the inflation process of the balloon of the treatment tool for the endoscope according to the first embodiment of the present invention.
Figure 6:
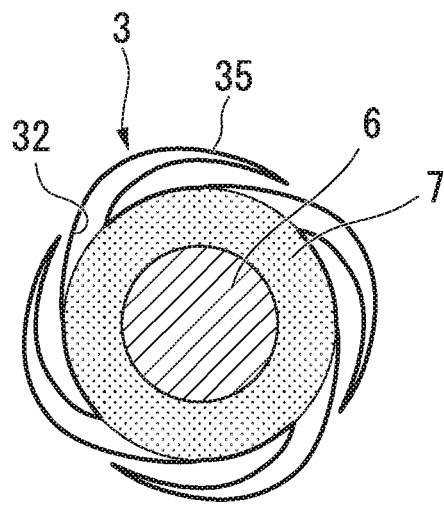
FIG. 6 is a cross-sectional view of the treatment tool for the endoscope according to the first embodiment of the present invention taken along arrow A-A line in FIG. 4.
Figure 7:
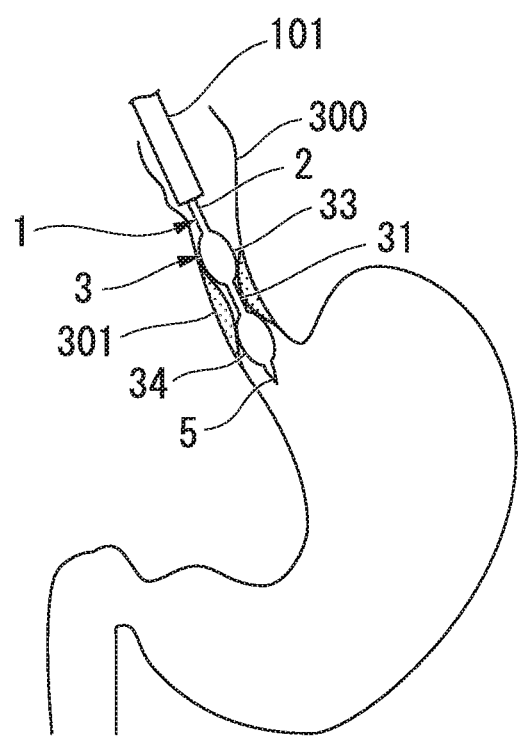
FIG. 7 is a view illustrating the usage mode of the treatment tool for the endoscope according to the first embodiment of the present invention.

FIG. 4 is a schematic view illustrating the inflation process of the balloon 3 of the treatment tool for the endoscope 1. FIG. 5 is a schematic view illustrating the inflation process of the balloon 3 of the treatment tool for the endoscope 1 and also illustrating a cross section in the direction of the longitudinal axis L corresponding to FIG. 4. FIG. 6 is a cross-sectional view of the treatment tool for the endoscope 1 taken along line A-A in FIG. 4. FIG. 7 is a view illustrating the usage mode of the treatment tool for the endoscope 1 according to the present embodiment.

As illustrated in (A) of FIG. 4 and FIG. 6, in the initial reduced diameter state, the wing-shaped portion 35 is wound around the stylet 6. Further, in the reduced diameter state, due to the adhering strength of the adhering portion 7, the inner surface 32 of the central portion 31 of the balloon 3 is in close contact with the adhering portion 7, as shown in (A) of FIG. 5. Furthermore, in (A) of FIG. 5, illustration of the wing-shaped portion 35 of the central portion 31 is omitted. When the balloon 3 and the sheath 2 are inserted into and removed from the insertion portion 101 of the endoscope 100 or when the balloon 3 is advanced and disposed into the stenosed portion or the like, the balloon 3 is kept in the reduced diameter state.

As illustrated in FIG. 2, a surgeon inserts the insertion portion 101 of the endoscope 100 into the patient P from his/her mouth and advances it to the vicinity of the stenosed portion 301 of the esophagus 300, as illustrated in FIG. 7. The surgeon places a distal end of the insertion portion 101 in the vicinity of the stenosed portion 301 while confirming the stenosed portion 301 of the esophagus 300 with an image obtained by the imaging part 103 of the endoscope 100.

Figure 8:
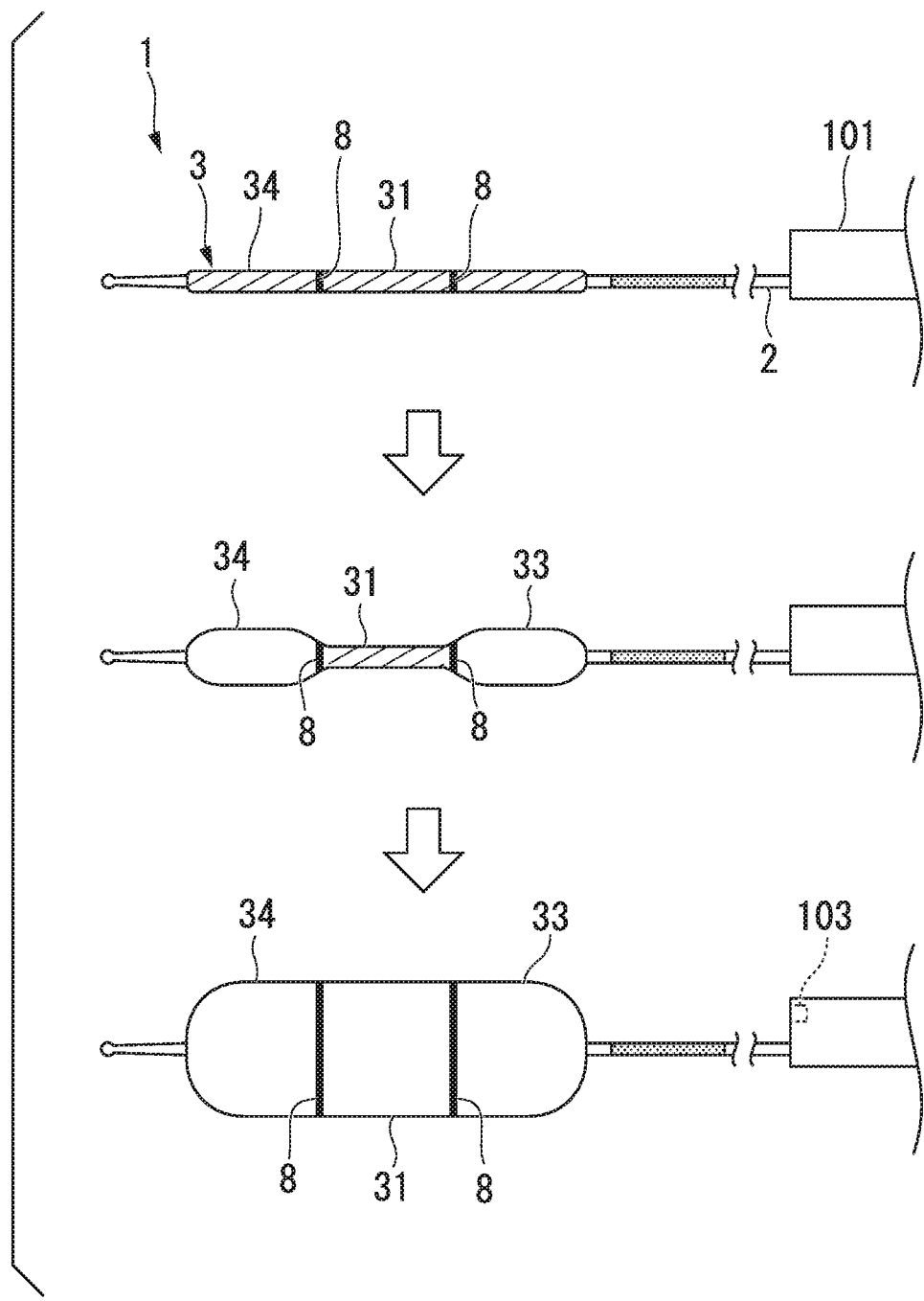
FIG. 8 is a side view illustrating the balloon in a modified example of the first embodiment.

In this state, the surgeon inserts the treatment tool for the endoscope 1, in which the inflator 200 is connected to the connecting portion 4, from the forceps opening 102 of the endoscope 100. The treatment tool for the endoscope 1 is caused to protrude from a channel of the insertion portion 101 of the endoscope 100 to place the balloon 3 such that the central portion 31 of the balloon 3 is located in the stenosed portion 301, the proximal end portion 33 is located closer to a proximal end side from the stenosed portion 301, and the distal end portion 34 is located closer to a distal end side from the stenosed portion 301. At this time, as illustrated in FIG. 8, when the visual marker 8 visible by the imaging part 103 of the endoscope 100 is provided at a boundary between the central portion 31 and the distal end portion 34 of the balloon 3 and at a boundary between the central portion 31 and the proximal end portion 33 thereof, the surgeon is capable of easily recognizing a position of the central portion 31 and smoothly perform an operation of placing the balloon 3 at an appropriate position.

Subsequently, the surgeon operates the inflator 200 to slowly inject the fluid such as distilled water into the balloon 3. When the distilled water (fluid) is injected from the inflator 200 into the balloon 3 in the reduced diameter state, a portion of the proximal end portion 33 folded in a wing shape and located on the proximal end side from the central portion 31 of the balloon 3 opens and starts to inflate. At this time, since a part of the inner surface 32 of the central portion 31 of the balloon 3 is in close contact with the adhering portion 7, the central portion 31 does not inflate, the fluid flows into the wing-shape portion 35 illustrated in FIG. 6, and the distal end portion 34 located on the distal end side from the central portion 31 also inflates. At this time, an internal pressure of the balloon 3 is gradually increased by the injection of the fluid.

Until the internal pressure of the balloon 3 reaches a predetermined first internal pressure after the injection of the fluid into the balloon 3 is started, the distal end portion 34 and the proximal end portion 33 of the balloon 3 inflate, but the sticking of the central portion 31 and the adhering portion 7 is held, as illustrated in (B) of FIG. 4 and (B) of FIG. 5. Therefore, an outer diameter of the central portion 31 of the balloon 3 is kept smaller than an outer diameter of each of the distal end portion 34 and the proximal end portion 33. That is, in a state in which the internal pressure of the balloon 3 is equal to or lower than the first internal pressure, a difference between the outer diameters r1 and r2 of the distal end portion 34 and the proximal end portion 33 and the outer diameter r3 of the central portion 31 increases as the fluid is injected. At this time, since the distal end portion 34 and the proximal end portion 33 of the balloon 3 inflate on both sides of the stenosed portion 301, it is possible to prevent the treatment tool for the endoscope 1 from being displaced with respect to the stenosed portion 301. The internal pressure of the balloon 3 is capable of being confirmed by a pressure gauge 202 (refer to FIG. 2) provided in the inflator 200. The surgeon is capable of confirming an inflated state of the balloon 3 by the image obtained by the imaging part 103 and the pressure gauge 202 of the inflator 200.

When the injection of the fluid is continued and the internal pressure of the balloon 3 becomes higher than the first internal pressure, the inner surface 32 of the central portion 31 is peeled off from the adhering portion 7, and the stuck state between the inner surface 32 and the adhering portion 7 is released. As a result, the central portion 31 inflates (increases in diameter) as the fluid flows in. When the injection of the fluid is continued, the central portion 31 inflates until the outer diameters r1 and r2 of the distal end portion 34 and the proximal end portion 33 and the outer diameter r3 of the central portion 31 become equal to each other, as illustrated in (C) of FIG. 4 and (C) of FIG. 5.

The balloon 3 formed of the film made of the material such as polyamide-based resin inflates by being unfolded while inflating until the outer diameters r1 and r2 of the distal end portion 34 and the proximal end portion 33 and the outer diameter r3 of the central portion 31 become equal to each other. At this time, the film itself forming the balloon 3 is hardly stretched. However, when the fluid is further injected into the balloon 3 after the folding is released, the internal pressure of the balloon 3 further increases and reaches a second internal pressure. In this case, as illustrated in (D) of FIG. 4 and (D) of FIG. 5, as the film constituting the balloon 3 is stretched, the entire balloon 3 inflates and a diameter thereof increases further than the aforementioned outer diameters r1, r2 and r3. As a result, since the balloon 3 inflates with a sufficient tension, the stenosed portion 301 or the like is capable of being dilated by the balloon 3.

After completion of the dilation operation, the fluid in the balloon 3 is suctioned by the inflator 200. As the fluid is suctioned, the balloon 3 deflates and is folded in the wing shape and returns to the reduced diameter state. Then, the treatment tool for the endoscope 1 is drawn into the channel of the insertion portion 101 of the endoscope 100 and removed from the endoscope 100.

According to the treatment tool for the endoscope 1 according to the embodiment, upon the inflation of the balloon 3, the distal end portion 34 and the proximal end portion 33 first increase in diameter when the balloon 3 is disposed in the stenosed portion 301 or the like and inflated, and thus it is possible to prevent a displacement of the treatment tool for the endoscope 1 with respect to the stenosed portion 301.

According to the treatment tool for the endoscope 1 according to the embodiment, since the central portion 31 of the balloon 3 is capable of being kept in the reduced diameter state by providing the adhering portion 7, the displacement of the balloon 3 is capable of being suitably prevented without preparing a balloon having a special shape or structure. Further, since physical properties at portions of the balloon 3 are not different, after the central portion 31 is peeled off from the adhering portion 7, it is possible to easily inflate the balloon 3 uniformly.

In the embodiment, the case in which the fluid is injected and suctioned only from the proximal end side of the balloon 3 has been exemplified, but the method of injecting the fluid into the balloon 3 is not limited thereto.

Figure 9:
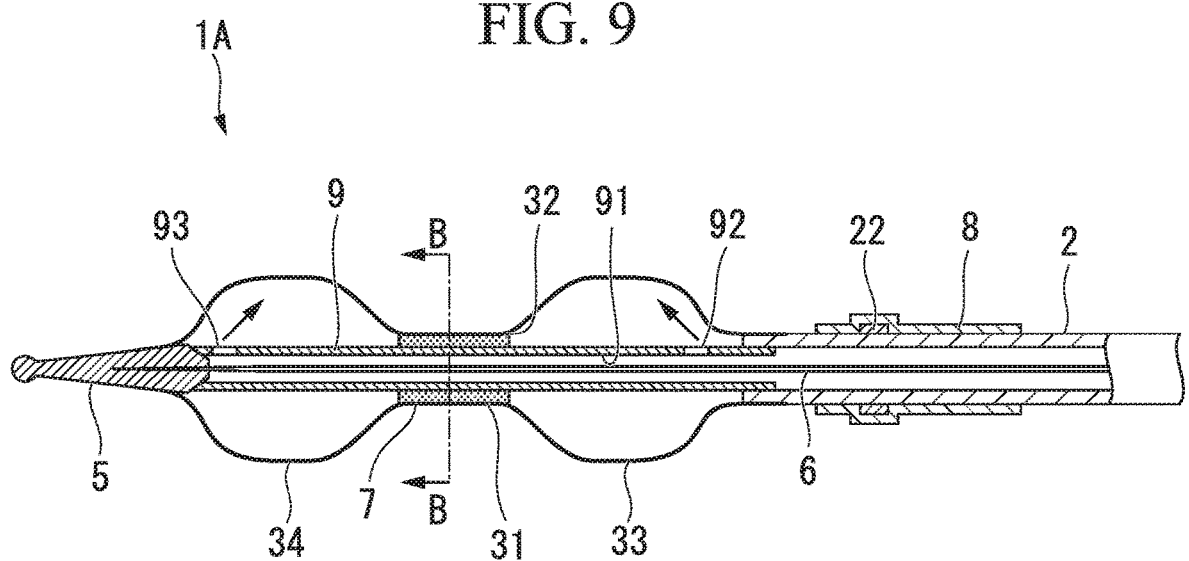
FIG. 9 is a cross-sectional view illustrating the balloon in the modified example of the first embodiment.
Figure 10:
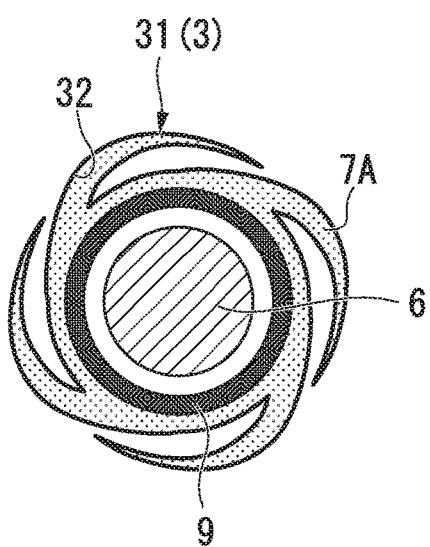
FIG. 10 is a cross-sectional view taken along arrow B-B illustrated in FIG. 9.

In a treatment tool for an endoscope 1A of a modified example illustrated in FIG. 9, a tube 9 is connected to a distal end of the sheath 2 and inserted into the balloon 3. A lumen 91 of the tube 9 communicates with the lumen 21 of the sheath 2. A distal end of the tube 9 is connected to the distal end tip 5. A first port 92 and a second port 93 communicating with the lumen 91 of the tube 9 are provided at a distal end portion and a proximal end portion of the tube 9. The first port 92 is located on the proximal end side from the adhering portion 7 in the direction of the longitudinal axis L. The second port 93 is located on the distal end side from the adhering portion 7 in direction of the longitudinal axis L. The stylet 6 is inserted through an inside of the tube 9. The adhering portion 7 is a substantially central portion in the direction of the longitudinal axis L of the tube 9 and is provided between the first port 92 and the second port 93. Other configurations are the same as those in the first embodiment. Further, as illustrated in a cross-sectional view of FIG. 10, the adhering material may be applied between an outer surface of the tube 9 and the inner surface 32 of the central portion 31 of the balloon 3 without a gap, thereby forming an adhering portion 7A. In this case, since the adhering force is increased by increasing an amount of the adhering material applied and also the fluid does not flow into the adhering portion 7A, the inflation of the central portion 31 of the balloon 3 is capable of being effectively suppressed.

In the treatment tool for the endoscope 1A of the modified example, when the fluid is injected from the inflator 200, the fluid is supplied from the lumen 21 of the sheath 2 into the lumen 91 of the tube 9, and the fluid is injected into the balloon 3 from the first port 92 and the second port 93. That is, the fluid is injected and suctioned from the distal end side and the proximal end side of the balloon 3. Therefore, in the reduced diameter state in which the inner surface 32 of the central portion 31 of the balloon 3 and the adhering portion 7 are in close contact with each other, the distal end portion 34 and the proximal end portion 33 of the balloon 3 smoothly inflate in a well-balanced manner. Therefore, it is possible to more reliably prevent the balloon 3 from being displaced with respect to the stenosed portion 301 or the like when the balloon 3 inflates.

Figure 11:
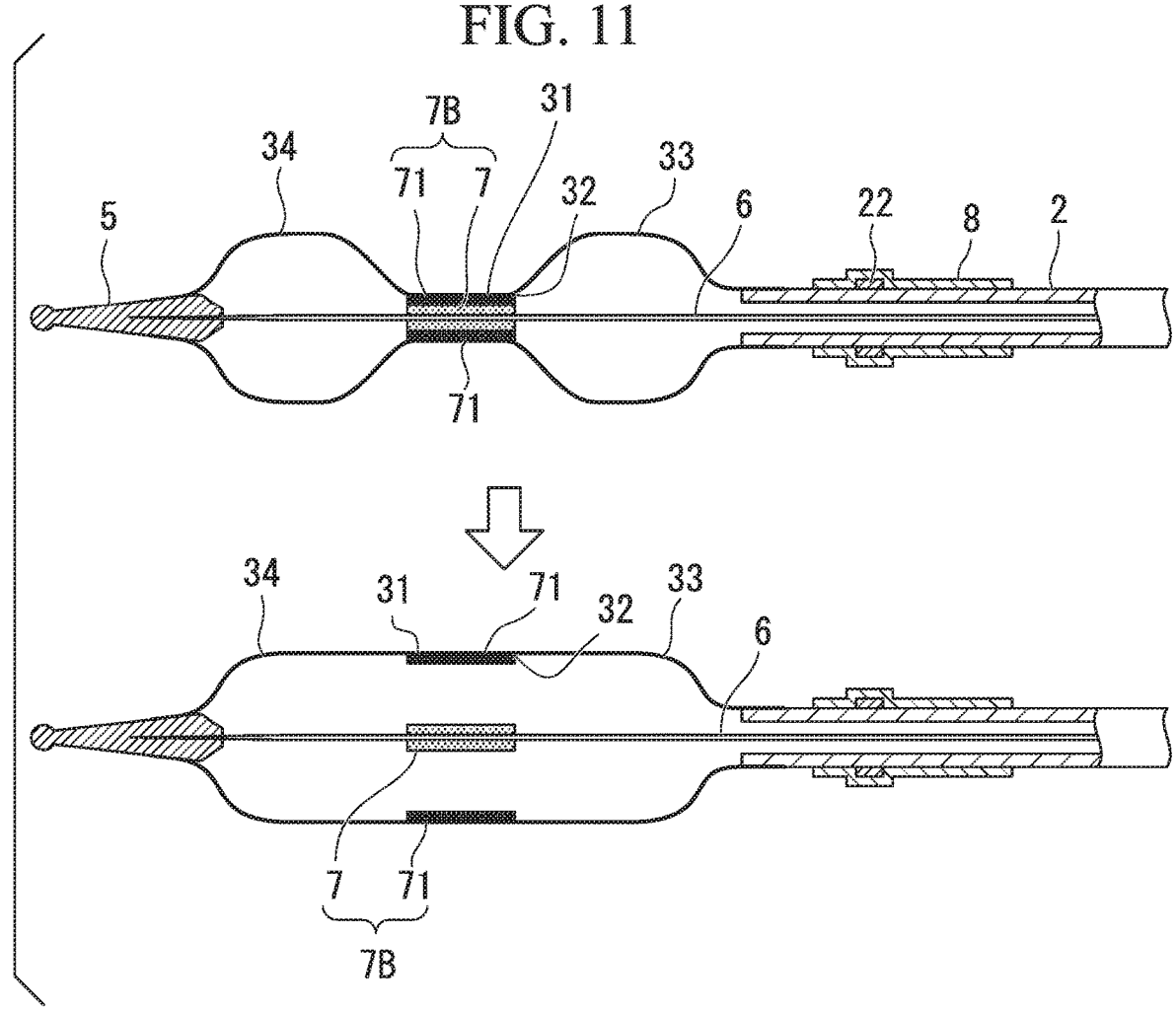
FIG. 11 is a cross-sectional view illustrating the balloon in the modified example of the first embodiment.

In the embodiment, although the example in which the adhering portion 7 is provided on the stylet 6 has been described, the adhering portion 7 is not limited thereto as long as the inner surface 32 of the central portion 31 of the balloon 3 is kept in the reduced diameter state. For example, as illustrated in FIG. 11, the adhering material may be applied to both of the stylet 6 and the inner surface 32 of the central portion 31 of the balloon 3 to form an adhering portion 7B. In this case, it is preferable that a transparent adhering material be used so that an adhering portion 71 provided on a side of the balloon 3 does not disturb the visual field of the imaging part 103 of the endoscope 100 after the balloon 3 inflates.

Figure 12:
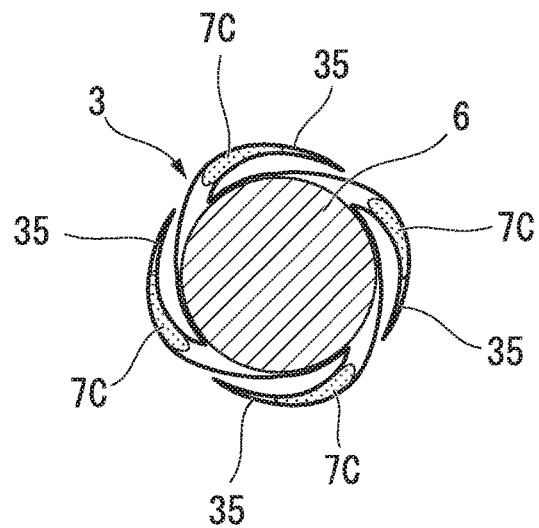
FIG. 12 is a cross-sectional view of the modified example of the first embodiment.

Another modified example of the adhering portion is illustrated in FIG. 12. FIG. 12 is a cross-sectional view of the central portion 31 orthogonal to the direction of the longitudinal axis L of the balloon 3 and the stylet 6. In the modified example illustrated in FIG. 12, an adhering portion 7C is provided between the inner surfaces 32 of the wing-shaped portions 35 of the balloon 3 when the diameter thereof is reduced. As described above, by providing the adhering portion 7C on the wing-shaped portion 35 of the balloon 3, it is also possible to cope with a case in which no shaft member such as the stylet 6 is provided, or a case in which the adhering member is not provided on the shaft member.

In the embodiment, the example in which the marker 8 is provided on the balloon 3 has been described, but the marker 8 may not be provided. Further, in the embodiment, although the distilled water is used as the fluid, the fluid may be a gas or another liquid as long as it is capable of inflating the balloon 3 and does not affect the human body.

Second Embodiment

Next, a second embodiment of the present invention will be described with reference to FIG. 13 and FIG. 14. A treatment tool for an endoscope 1B according to the second embodiment includes a guide wire 11, and is capable of being suitably used when it is difficult for the balloon to be inserted into the occluded portion or the like. The treatment tool for the endoscope 1B according to the second embodiment is different from the first embodiment in configurations of the distal end tip, the shaft member and the sheath. In the following description, the same reference numerals are given to configurations and so on in common with those already described, and redundant descriptions are omitted.

Figure 13:
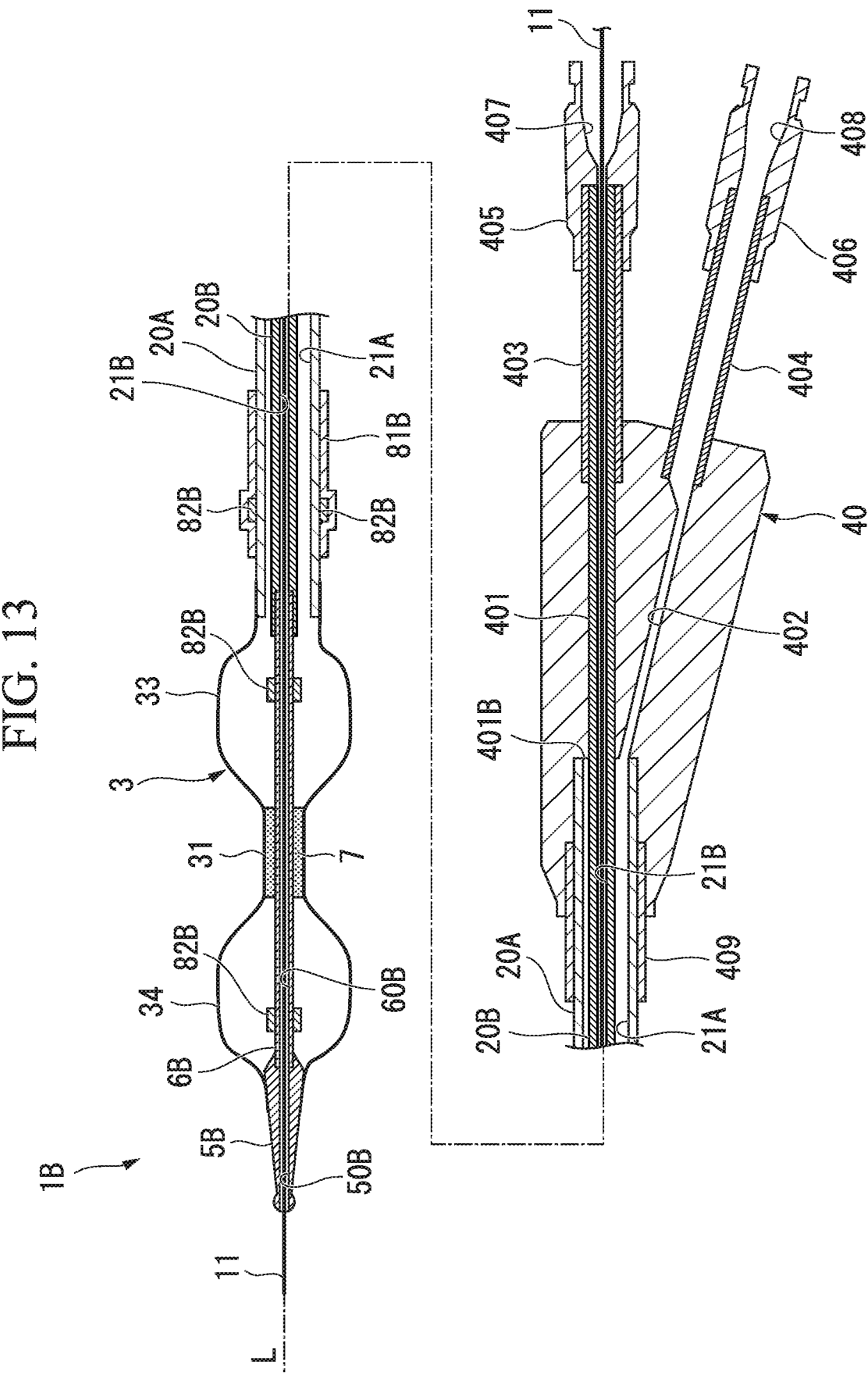
FIG. 13 is a cross-sectional view illustrating a treatment tool for an endoscope according to a second embodiment of the present invention.
Figure 14:
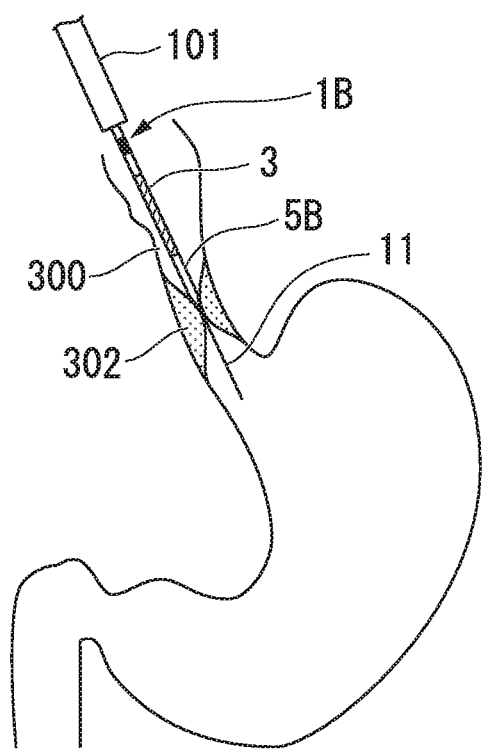
FIG. 14 is a view illustrating a usage mode of the treatment tool for the endoscope according to the second embodiment of the present invention.

FIG. 13 is a cross-sectional view of the treatment tool for the endoscope 1B in the direction of the longitudinal axis L. The treatment tool for the endoscope 1B includes a sheath composed of an outer sheath 20A and an inner sheath 20B. A distal end of the outer sheath 20A is fixed to the balloon 3. A visual marker 81B visible on an image of the imaging part 103 and an X-ray marker 82B capable of being confirmed by an X-ray image are provided at a distal end portion of the outer sheath 20A.

The inner sheath 20B is inserted through the outer sheath 20A. An inner tube 6B is connected to a distal end of the inner sheath 20B. The X-ray marker 82B capable of being confirmed by the X-ray image is provided on the distal end side and the proximal end side of the inner tube 6B. An insertion passage 50B passing through a distal end tip 5B in the direction of the longitudinal axis L is formed in the distal end tip 5B. The insertion passage 50B of the distal end tip 5B, a lumen 60B of the inner tube 6B and a lumen 21B of the inner sheath 20B communicate with each other.

The proximal end sides of the outer sheath 20A and the inner sheath 20B are connected to a branch cover 40. The branch cover 40 includes a main lumen 401 extending in the direction of the longitudinal axis L and a subsidiary lumen 402 branched from a middle of the main lumen 401 and extending toward the proximal end side in a direction intersecting the longitudinal axis L. A tubular first connector arm 403 communicating with the main lumen 401 is connected to a proximal end side of the main lumen 401. A proximal end portion of the first connector arm 403 is connected to a first connector 405. A communication passage 407 extending in the direction of the longitudinal axis L is formed in the first connector 405. A tubular second connector arm 404 communicating with the subsidiary lumen 402 is connected to a proximal end portion of the subsidiary lumen 402.

The outer sheath 20A and the inner sheath 20B are inserted into the branch cover 40 together in a state in which the inner sheath 20B is inserted into the outer sheath 20A. A proximal end of the outer sheath 20A is in contact with a wall portion 401B formed in a branch portion between the main lumen 401 and the subsidiary lumen 402 in the branch cover 40. A lumen 21A of the outer sheath 20A, the subsidiary lumen 402, a lumen of the second connector arm 404, and a communication passage 408 of the second connector 406 communicate with each other. The main lumen 401 is reduced in diameter at the branch portion. The inner sheath 20B extending from the proximal end of the outer sheath 20A is inserted into a reduced diameter portion of the main lumen 401. In the wall portion 401B, a space between the reduced diameter portion of the main lumen 401 and the inner sheath 20B is sealed with a sealing material (not illustrated) to prevent inflow of a fluid. The inner sheath 20B is inserted through the first connector arm 403 and connected to the first connector 405. The lumen 21B of the inner sheath 20B communicates with the communication passage 407 of the first connector 405.

In a connecting portion between the outer sheath 20A and the branch cover 40, the outer sheath 20A is covered with a cladding tube 409, and a proximal end side of the cladding tube 409 is inserted into the branch cover 40 together with the outer sheath 20A. The cladding tube 409 is capable of preventing the outer sheath 20A from being broken and damaged at the connecting portion with the branch cover 40.

The guide wire 11 is provided in the treatment tool for the endoscope 1B. The guide wire 11 is inserted from the first connector 405 and is also inserted through the lumen 21B of the inner sheath 20B, the inner lumen 60B of the inner tube 6B and the insertion passage 50B to be capable of protruding from a distal end of the insertion passage 50B of the distal end tip 5B.

The second connector 406 is connected to the cap 201 of the inflator 200 illustrated in FIG. 2. The fluid supplied from the inflator 200 is capable of being injected into the balloon 3 through the lumen of the second connector arm 404, the subsidiary lumen 402, and a space between the outer sheath 20A and the inner sheath 20B.

The adhering portion 7 is provided at a substantially central portion of the inner tube 6B in the direction of the longitudinal axis L. The configuration for keeping the central portion 31 of the balloon 3 in the reduced diameter state by the adhering portion 7 is the same as that in the first embodiment.

Next, a method of using the treatment tool for the endoscope 1B will be described by exemplifying a case in which the treatment tool for the endoscope 1B is applied to the endoscopic dilation operation of the occluded portion 302 of the inner cavity. FIG. 14 is a view illustrating the usage mode of the treatment tool for the endoscope 1B according to the second embodiment. First, the insertion portion 101 of the endoscope 100 is inserted to the occluded portion 302 in the body.

The surgeon causes the treatment tool for the endoscope 1B to protrude from a channel (not illustrated) of the insertion portion 101 while visually confirming the position of the occluded portion 302 based on the image obtained by the imaging part 103 and sequentially causes the guide wire 11 to protrude from the distal end of the distal end tip 5B and to enter the occluded portion 302 of the esophagus 300.

When the guide wire 11 is inserted to the distal end side of the occluded portion 302 and the distal end tip 5B and the balloon 3 are advanced with respect to the guide wire 11 while a position of the guide wire 11 is held, the balloon 3 is inserted through the occluded portion 302. The surgeon adjusts the position of the balloon 3 while confirming the visual marker 81B. When it is difficult to visually confirm, the balloon 3 is capable of being placed at an appropriate position with respect to the occluded portion 302 by confirming the position of the X-ray marker 82B with the X-ray image. Since the subsequent inflation process of the balloon is the same as that in the first embodiment, the description thereof is omitted.

According to the treatment tool for the endoscope 1B of the second embodiment, the same advantage as that of the first embodiment is obtained.

Further, according to the treatment tool for the endoscope 1B of the second embodiment, since the visual marker 81B and the X-ray marker 82B are provided, the balloon 3 is capable of appropriately being disposed even in the occluded portion 302 having poor visibility.

Further, according to the treatment tool for the endoscope 1B of the second embodiment, the balloon is capable of being smoothly disposed using the guide wire 11 even in a narrow gap such as the occluded portion.

Although the embodiments of the present invention have been described in detail with reference to the drawings, specific configurations are not limited to the embodiments, and design changes or the like within the scope not deviating from the gist of the present invention are included.

In addition, the elements described in each of the embodiments and each of the above-described modified examples are capable of being configured by appropriately combining them.

What is claimed is:

1. A treatment tool for an endoscope, comprising:
   a sheath;
   a balloon provided at the sheath and configured to be expandable to an inflated state from a reduced diameter state by injecting a fluid;
   a shaft member inserted through an inside of the balloon and configured to extend along a longitudinal axis of the sheath from a distal end of the balloon to a proximal end thereof; and
   an adhering portion provided on a side of an inner surface of a central portion of the balloon in a direction of the longitudinal axis, formed of an adhering material applied or adhered to the shaft member and configured to hold the central portion in a state in which the central portion is reduced in diameter,
   wherein the balloon is configured so that, when the fluid is injected and an internal pressure of the balloon is equal to or lower than a first internal pressure, the inner surface of the central portion is stuck to the shaft member by the adhering material, and only a distal end portion located on a distal end side from the central portion, and a proximal end portion located on a proximal end side from the central portion inflate so that a difference between an outer diameter of each of the distal end portion and the proximal end portion and, an outer diameter of the central portion increases, and when the internal pressure of the balloon is higher than the first internal pressure, the central portion is peeled off from the adhering portion, a state in which the central portion is reduced in diameter is released, the central portion increases in diameter, and thus the balloon has a substantially cylindrical shape.

2. The treatment tool for the endoscope according to claim 1, wherein, when the balloon returns to the reduced diameter state after the adhering material is peeled off from the balloon, the adhering material is stuck again to the balloon and holds the central portion in a state in which the central portion is reduced in diameter.

3. The treatment tool for the endoscope according to claim 1, wherein the shaft member has a first port and a second port configured to inject the fluid injected from the sheath into the balloon, the first port is located on a proximal end side from the adhering portion in the direction of the longitudinal axis, and the second port is located on a distal end side from the adhering portion in the direction of the longitudinal axis.

4. The treatment tool for the endoscope according to claim 1, wherein a marker is provided at an end portion of the central portion of the balloon in the direction of the longitudinal axis.

5. The treatment tool for the endoscope according to claim 1, wherein the reduced diameter state is a state in which the distal end portion, the proximal end portion and the central portion of the balloon are folded, the inflated state is a state in which folds of the distal end portion, the proximal end portion and the central portion of the balloon are released, and the balloon increases in diameter due to the release of the folds until reaching the inflated state, and when the fluid is further injected and the internal pressure is increased in the inflated state, a film constituting the balloon is stretched, and thus the distal end portion, the proximal end portion and the central portion further inflate.

6. A treatment tool for an endoscope, comprising:

a sheath;

a balloon provided at the sheath and configured to be expandable to an inflated state from a reduced diameter state by injecting a fluid; and an adhering portion provided on a side of an inner surface of a central portion in a direction of a longitudinal axis of the sheath, and configured to hold the central portion in a state in which the central portion is reduced in diameter, wherein the inflated state is a state in which folds of a distal end portion, a proximal end portion and the central portion are released, wherein the reduced diameter state is a state in which the distal end portion, the proximal end portion and the central portion of the balloon are folded, and wherein the balloon is configured so that, when the fluid is injected and an internal pressure of the balloon is equal to or lower than a first internal pressure, sticking of the central portion and the adhering portion is held, and only the distal end portion and the proximal end portion inflate, when the internal pressure of the balloon is higher than the first internal pressure, the adhering portion is peeled off, the central portion inflates, and thus the balloon expands to the inflated state, and when the fluid is further injected and the internal pressure is increased in the inflated state, a film constituting the balloon is stretched, and thus the distal end portion, the proximal end portion and the central portion further inflate.

7. The treatment tool for the endoscope according to claim 6, wherein, when the balloon returns to the reduced diameter state after the adhering portion is peeled off from the balloon, the adhering portion is stuck again to the balloon and holds the central portion in a state in which the central portion is reduced in diameter.

8. The treatment tool for the endoscope according to claim 6, further comprising a shaft member inserted through an inside of the balloon and configured to extend along the longitudinal axis from a distal end of the balloon to a proximal end thereof, wherein the adhering portion is applied or adhered to the shaft member, wherein the shaft member has a first port and a second port configured to inject the fluid injected from the sheath into the balloon, the first port is located on a proximal end side from the adhering portion in the direction of the longitudinal axis, and the second port is located on a distal end side from the adhering portion in the direction of the longitudinal axis.

9. The treatment tool for the endoscope according to claim 6, wherein a marker is provided at an end portion of the central portion of the balloon in the direction of the longitudinal axis.

* * * * *